(12) United States Patent
Kim

(10) Patent No.: US 7,472,603 B2
(45) Date of Patent: Jan. 6, 2009

(54) EVALUATING METHOD OF THE RESIDUAL STRESS DETERMINING METHOD USING THE CONTINUOUS INDENTATION METHOD

(75) Inventor: Kwang Ho Kim, Seoul (KR)

(73) Assignees: Frontics, Inc. (KR); Won Seok Jung (KR)

( * ) Notice: Subject to any disclaimer, the term of this patent is extended or adjusted under 35 U.S.C. 154(b) by 21 days.

(21) Appl. No.: 11/793,274

(22) PCT Filed: Nov. 22, 2005

(86) PCT No.: PCT/KR2005/003947

§ 371 (c)(1),
(2), (4) Date: Jun. 15, 2007

(87) PCT Pub. No.: WO2006/071001

PCT Pub. Date: Jul. 6, 2006

(65) Prior Publication Data

US 2008/0141782 A1      Jun. 19, 2008

(30) Foreign Application Priority Data

Dec. 16, 2004   (KR) .................. 10-2004-0106759

(51) Int. Cl.
*G01N 11/00* (2006.01)
(52) U.S. Cl. ............... 73/823; 73/81; 73/789; 73/799; 73/804
(58) Field of Classification Search .......... 73/81, 73/789, 799, 804, 823
See application file for complete search history.

(56) References Cited

U.S. PATENT DOCUMENTS 5,146,779 A * 9/1992 Sugimoto et al. ............ 73/81
5,432,595 A * 7/1995 Pechersky ................ 356/35.5

(Continued)

FOREIGN PATENT DOCUMENTS

JP     05-079928 A     3/1993

OTHER PUBLICATIONS

International Search Report for PCT/KR2005/003947 dated Mar. 7, 2006 (in English).

*Primary Examiner*—Edward Lefkowitz
*Assistant Examiner*—Freddie Kirkland, III
(74) *Attorney, Agent, or Firm*—Harness, Dickey & Pierce, P.L.C.

(57) ABSTRACT

The present invention relates to a method of measuring residual stress and, more particularly, to a residual stress measuring method using a continuous indentation tester. Due to pile-up and sink-in of a material or a blunted tip, a conventional residual stress measuring method cannot compensate for error of a real contact (indentation) depth or directly remove stress through a thermal or mechanical technique in the conventional method of measuring residual stress of a weldment, so that it is very difficult to estimate a stress-free reference curve or to quantitatively measure residual stress. However, the present invention can precisely estimate a stress-free curve of a weldment using an indentation strength ratio (OIT ratio) of a stress-free base metal to the weldment, and compensates for error, occurring in the measurement of a material having a weldment or an anisotropic stress structure, based on the indentation strength ratio, thereby more precisely measuring residual stress. Thus, unlike the conventional method, the present method can minimize error occurring in the residual stress measuring process, and agrees with actual models.

14 Claims, 8 Drawing Sheets

U.S. PATENT DOCUMENTS

| | | |
|---|---|---|
| 5,463,896 A | 11/1995 | Abbate et al. |
| 6,155,104 A * | 12/2000 | Suresh et al. ............... 73/81 |
| 6,311,135 B1 | 10/2001 | Suresh et al. |
| 6,470,756 B1 * | 10/2002 | Prime ....................... 73/799 |
| 6,568,250 B1 | 5/2003 | Sinha |

* cited by examiner

Fig. 4
| Materials | YS(MPa) | n | E (GPa) (Ultrasonic) | Poisson' ratio | Er | f |
|---|---|---|---|---|---|---|
| SUJ2 | 306.8 | 0.268 | 214.9 | 0.286 | 194.4 | 1.03 |
| X65 | 451.8 | 0.161 | 204.2 | 0.300 | 187.6 | 1.10 |
| X70 | 592.9 | 0.129 | 185.9 | 0.296 | 180.9 | 1.12 |
| SKD61 | 348.9 | 0.303 | 211.5 | 0.268 | 190.0 | 1.00 |
| SCM21 | 290.2 | 0.221 | 199.4 | 0.300 | 184.0 | 1.07 |
| SKH51 | 263 | 0.315 | 246.8 | 0.241 | 213.3 | 1.00 |
| KP3 | 763.7 | 0.124 | 203.1 | 0.295 | 186.2 | 1.12 |
| SKD11 | 243.4 | 0.338 | 215.7 | 0.294 | 195.8 | 0.98 |
| SK3 | 244.1 | 0.264 | 198.2 | 0.303 | 183.4 | 1.04 |
| SCM4 | 592.4 | 0.141 | 207.1 | 0.286 | 188.5 | 1.11 |
| S45C | 372.9 | 0.333 | 209.1 | 0.287 | 190.1 | 0.98 |
| SK4 | 336.1 | 0.252 | 209.2 | 0.291 | 190.5 | 1.04 |
| SUS304 | 398.8 | 0.3 | 198.7 | 0.283 | 181.7 | 1.00 |
| SUS316 | 357.2 | 0.276 | 198.5 | 0.298 | 183.1 | 1.02 |
| SUS303 | 264.4 | 0.39 | 188.1 | 0.301 | 175.3 | 0.94 |
| A106 | 332.6 | 0.223 | 199.6 | 0.292 | 183.4 | 1.06 |
| Al20 | 206.5 | 0.243 | 65.0 | 0.352 | 69.7 | 1.04 |
| Al50 | 82.9 | 0.287 | 70.9 | 0.338 | 74.8 | 1.02 |
| Al70 | 526.2 | 0.089 | 66.0 | 0.343 | 70.2 | 1.11 |
| | | | | | Average : | 1.04 |
Fig. 5
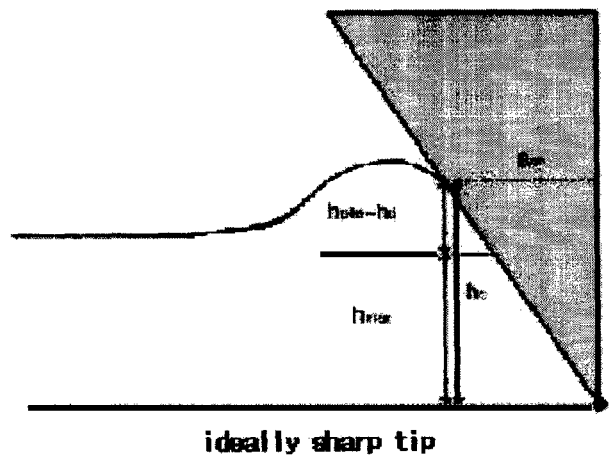
ideally sharp tip
Fig. 6
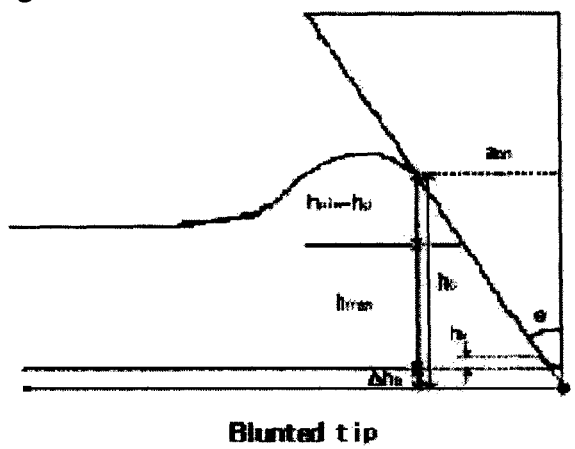
Blunted tip Ideal : $h_c = 7d$ Real : $h_c \neq 7d$ Fig. 13
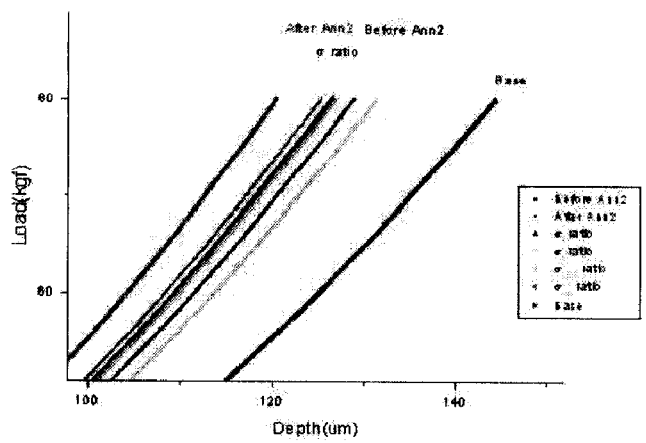
Fig. 14
| sample | residual stress | | $\sigma_{YS}$ | $\sigma_r$ | $\sigma_f$ | $\sigma_{UTS}$ | remark |
|---|---|---|---|---|---|---|---|
| A | X | AVERAGE | 486.6 | 615.8 | 583.6 | 680.5 | |
| | O (100MPa) | AVERAGE | 449.6 | 603.2 | 570.6 | 691.6 | |
| | O | AVERAGE | 452.6 | 599.1 | 568.4 | 684.3 | |
| | Error (%) | | 8.2 | 2.1 | 2.3 | -1.6 | |
| | Error (%) | | 7.5 | 2.8 | 2.7 | -0.5 | |
Fig. 15
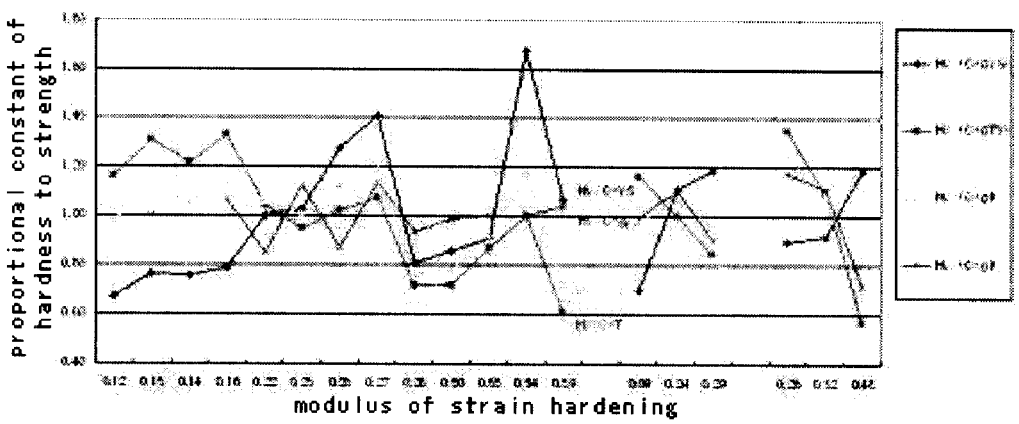

EVALUATING METHOD OF THE RESIDUAL STRESS DETERMINING METHOD USING THE CONTINUOUS INDENTATION METHOD

TECHNICAL FIELD

The present invention relates to a method of measuring residual stress and, more particularly, to a method of measuring residual stress using a continuous indentation tester, in which an error caused by pile-up or sink-in of a material or a blunted tip is compensated for precisely measuring residual stress.

BACKGROUND ART

In the related art, a method of measuring residual stress present in a specimen while applying a load to the specimen after picking up the specimen from material has been proposed and used. Particularly, a destructive method of measuring residual stress, in which a specimen is picked up from material to measure residual stress, cannot be used for the measurement of residual stress of buildings or industrial facilities which are actually in use, so that it is necessary to use a nondestructive method to measure the residual stress.

Thus, a technique of evaluating residual stress through repeatedly loading and unloading the surface of a material, measuring indentation load and depth, and measuring residual stress of the material based on the indentation load and depth has been proposed and used.

Korean Patent Registration No. 0416723, which was filed by and issued to the applicant of the present invention, disclosed "Apparatus for Measuring Residual Stress, Methods of Measuring Residual Stress and Residual Stress Data Using the Apparatus, and Recording Medium for Storing Software for the Residual Stress Measuring Method".

The conventional apparatus and method for measuring residual stress of a material will be described herein below with reference to FIG. 1. In order to measure residual stress, an indentation load-depth curve of a reference specimen (stress-free state) is required. The reason for this is to compare an indentation load-depth curve of an actual specimen with that of the reference specimen. In order to measure residual stress, the following process must be executed, and the sequence thereof is described below.

First, continuous multiple indentation tests for the reference specimen are executed using the above-mentioned residual stress measuring apparatus. A fitted equation of a loading curve, the slope of an unloading curve, and an actual indentation depth $h_c$ are obtained based on the curves obtained from the tests.

Only loading curves which are free from mechanical relaxation, a deceleration/acceleration effect, and a creep effect are separated from the obtained indentation load-depth curves to execute a fitting process. This fitting process is required in order to accurately measure a value, because the shapes of unloading curves are distorted in the case of actual multiple indentations and so the curves are different from that of an actually applied load.

A load applied when Vickers indentation tests, indicating a certain hardness, are executed is proportional to an indentation area, but it is difficult to accept the load as being precisely proportional to the indentation area due to complicated elasticity/plastic strain under the indenter tip. Accordingly, the relationship between the indentation load and indentation depth given at the time of loading is fitted in the form of a fifth-order equation, as expressed in Equation 1, thus obtaining an experimental equation, $$L = a_1 h^5 + a_2 h^4 + a_3 h^3 + a_4 h^2 + a_5 h + c \quad \text{[Equation 1]}$$

wherein $a_1$, $a_2$, $a_3$, $a_4$, $a_5$, and c are constants.

Next, when each unloading curve is analyzed, each unloading curve is also fitted in the form of the following Equation 2 in the same manner as the analysis of the loading curves. Equation 2 is an algorithm for calculating the curve that is closest to all points on the unloading curves, $$L = k(h - h_f)^m \quad \text{[Equation 2]}$$

where $h_f$ is a final residual depth after the load is removed. When logs are taken of both terms of Equation 2 to carry out a fitting process, k and m can be obtained, and the slope S of the unloading curve can be obtained using k and m. The relationship of the slope S to k and m is defined in the following Equation 3.

$$S = \left(\frac{dL}{dh}\right)_{h=h_m} = km(h - h_f)^{m-1} \quad \text{[Equation 3]}$$

A real contact area between the indenter tip and the specimen is maintained while an elastic indentation load is removed, the unloading curve is linear, and a contact depth $h_c$ is determined from the linear unloading curve. However, the contact area decreases depending on the actual shape of the indenter tip while the load is removed, and elastic bending around the contact area also varies. A relationship indicating the contact between the indenter tip and the specimen can be expressed as the following Equation 4.

In Equation 3, the slope S is determined by taking a maximum displacement value on each unloading curve as $h_{max}$. After that, $h_{max}$ is reset to an intersection point between the curve of the equation obtained by fitting the loading curve and a tangent line of an unloading curve which can be obtained using the slope S in each loading curve. The reason for this is to minimize error generated in the case where each unloading curve deviates from an ideal shape as a result of equipment clearance.

$$h_c = h_{max} - \omega(h_{max} - h_1) = h_{max} - \omega \frac{L_{max}}{S} \quad \text{[Equation 4]}$$

In Equation 4, $h_i$ is an intercept depth when the tangent line of the unloading curve is extended, and $h_{max}$ is a maximum indentation depth in each unloading curve, obtained using the intersection point between the above loading curve and the tangent line of the unloading curve, which can be obtained using the slope S.

$\omega$ is a geometrical factor of the indenter tip and is given as 0.72 in the case of the Vickers indenter tip. Such contact depth determination is carried out for each unloading curve.

After the tests for the reference specimen have been completed, tests for specimens requiring the measurement of residual stress are carried out. In this case, there is no need to execute a partial load removing step, which is due to the fact that, since the relative difference between applied loads with respect to a certain indentation depth at each specimen is directly related to residual stress in each specimen, it is not necessary to obtain a value $h_c$ after a standardized indentation depth $h_c$ has been previously obtained from the reference specimen.

After continuous indentation tests have been carried out for specimens requiring the measurement of residual stress, a fitting procedure for a loading curve is executed in the same manner as that described for the reference specimen tests. An equation obtained through the fitting procedure is compared with the fitted equation obtained from the reference specimen. In this case, the sign of residual stress in each specimen can be determined through the shape of a measured indentation load-depth curve. That is, if the measured indentation load-depth curve is placed above that of the reference specimen, it can be determined that compressive residual stress exists; otherwise it can be determined that tensile residual stress exists.

After loading curve equations are obtained, residual stress is measured by relationships, which will be described later. It can be considered that the difference between indentation loads applied to the reference specimen and an actual specimen at the same indention depth is generated due to residual stress, so residual stress can be obtained by dividing the load difference by a real contact area. In this embodiment, the load difference was obtained at the indentation depth $h_{max}$ obtained from each unloading curve. Therefore, in a single test, a number of calculated residual stress values equal to the number of partial unloading times, obtained during the reference test, can be obtained.

A constant $\alpha$ exists because the distribution states of stresses present in the specimen are different, for example, in the case of a hydrostatic biaxial stressed state ($\sigma_x = \sigma_y$) on a thin film, or in the case where only a single directional stress is considered to be important ($\sigma_x >> \sigma_y$) like a weldment.

If the influence due to residual stress is indicated by a difference in an applied load at the same indentation depth, the stress value at that time can be expressed by the following Equation 5 because the stress value is obtained by dividing the applied load by a unit area, $$L_{res} = L - L_o$$ [Equaiton 5]

$$\sigma_{res} = \alpha \frac{L_{res}}{A_c}$$

where $L_{res} = L_0 - L = \Delta L$ where L is an indentation load applied to the actual specimen, $L_0$ is an indentation load applied to the reference specimen, and $A_c$ is a real contact area and is expressed as the following Equation 6 in consideration of the geometrical form of a Vickers indenter tip.

$$A_c = 24.5 h_c^2$$ [Equation 6]

If each value $A_c$ obtained by applying each $h_c$, obtained from the reference specimen to Equation 6, is applied to Equation 5, actual residual stress values vary within a predetermined range, which is due to the fact that, as the indentation load increases, the plastic area under the indenter tip increases.

Accordingly, residual stress is defined by the mean value obtained by averaging residual stress values corresponding to contact areas.

However, in the conventional method of measuring residual stress, a minute error may occur due to the difference between the ideal value obtained from ideal measurement and the actual value obtained from an actual test. In other words, when a graph having ideal indentation load-depth curves cannot be obtained, the indentation load may be underestimated or the displacement may be overestimated, so that an error may be generated.

Furthermore, in the related art, the slope of an unloading curve is obtained from the continuous indentation load-depth curve and is used to measure residual stress. However, a substantial error may occur between an ideal unloading curve and an actual unloading curve, so that it is necessary to eliminate the error.

In addition, the relationship between an applied indentation load with respect to a certain indentation depth while loading is appropriately converted from a complex fifth-order equation into a simple second-order equation which can generate a curve that agrees with an actual indentation curve. Furthermore, the conventional method of measuring residual stress cannot account for an error caused by a blunted tip, which has become blunt due to repeated tests, or by pile-up or sink-in of a material, so that measuring results may include an error. Thus, it is required to compensate for the error.

In addition, it is impossible to estimate a stress-free curve of an actual weldment in the stress-free state, so that an error may occur in the measuring results and must be compensated for.

In the related art, a stress-free curve can be obtained only from a reference specimen (stress-free state). It is impossible to adapt the stress-free curve to a specified region, such as a weldment, which has stresses acting in different directions or having different sizes. To obtain a stress-free curve, a stress-free state must be produced through mechanical or thermal techniques prior to measurement. In other words, a stress-free curve cannot be estimated from an actual weldment in a stress-free state, so that, if a stress-free curve is estimated from a material exhibiting an anisotropic stressed state in a weldment, an error may occur in measuring results and must be compensated for.

DISCLOSURE

[Technical Problem]

Accordingly, the present invention has been made keeping in mind the above problems occurring in the prior art, and an object of the present invention is to provide a method of measuring residual stress, in which an error caused by deformation of an indenter tip or by pile-up or sink-in of a material can be compensated for.

Another object of the present invention is to provide a method of measuring residual stress, in which a curve exhibiting the relationship between an indentation load and an indentation depth is simplified to be expressed as a second-order equation, the indentation depth and contact area are obtained from a loading curve to reduce an error caused by an actually measured curve, and a stress-free curve of a weldment in a stress-free state is estimated using a strength ratio, so that residual stress can be precisely measured.

[Advantageous Effects]

As is apparent from the above descriptions, the present invention is advantageous in that it provides a method of measuring residual stress, which can minimize error occurring in the residual stress measuring process and agrees with actual models.

Furthermore, according to the present invention, the conventional complex indentation curve is analyzed such that the dependent part, which has acted as a cause of error in analysis of the indentation curve, is analyzed using a loading curve that is an independent part. In addition, the present invention precisely calculates a contact area by measuring an actual indentation depth which can minimize an error caused by a blunted tip or the pile-up or sink-in of material, and measures residual stress of the material based on the measured contact area.

In the related art, it has been impossible to estimate the stress-free curve of a weldment or to measure the residual stress of the weldment without using a mechanical/thermal technique. However, in the present invention, the stress-free curve of a weldment can be precisely estimated using an indentation strength ratio ($\sigma_{IT}$ ratio) of a weldment to a residual stress-free base of the material. Thus, the present invention can quantitatively measure the residual stress of a material having a weldment or an anisotropic stress structure.

DESCRIPTION OF DRAWINGS

FIG. 4 is a table, in which contact depth (indentation depth) compensation constants f obtained from actual tests are given;

FIG. 5 is a sectional view of a material deformed by an ideally sharp tip, and

FIG. 6 is a sectional view of a material deformed by a blunted tip;

FIG. 13 is a graph illustrating comparison of stress-free curves of SS400, which were respectively induced through annealing and using an indentation strength ratio;

FIG. 14 is a table, in which amounts of change in the indentation strength according to the size of residual stress are given;

FIG. 15 is a graph illustrating the ratio of indentation strength to indentation hardness by modulus of strain hardening (or by material);

BEST MODE

Figure 1:
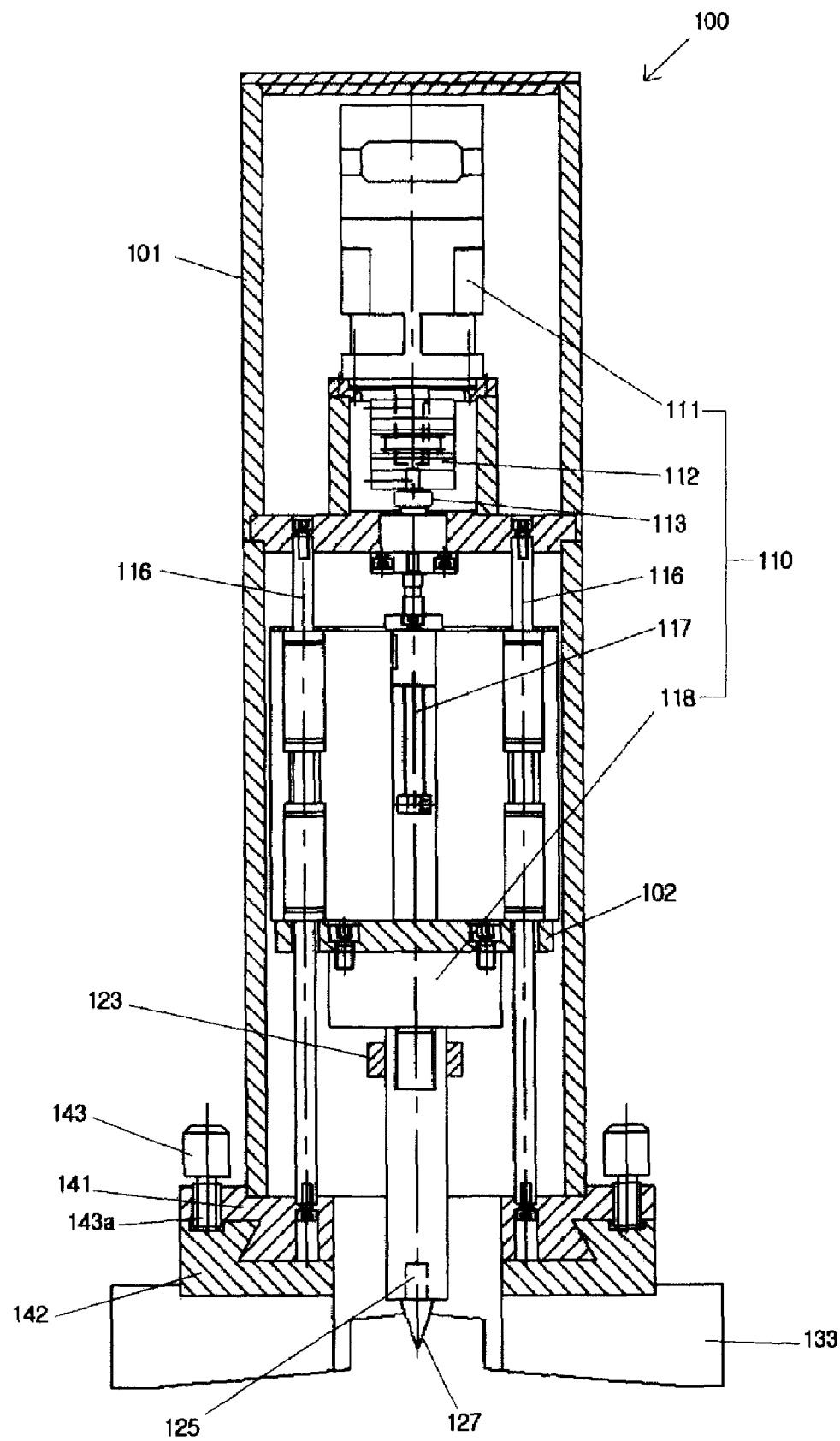
FIG. 1 is a front sectional view of the body of a conventional apparatus for measuring residual stress.

In order to accomplish the objects of the present invention, there is provided a method of measuring residual stress of material using a continuous indentation technique, comprising the steps of: repeatedly applying and removing an indentation load to and from a reference specimen of the material in a stress-free state, thus generating an indentation load-depth curve in a stress-free state, measuring a maximum indentation load and a maximum indentation depth from the indentation load-depth curve in a stress-free state, calculating an actual indentation depth $h_c$ from the maximum indentation depth and calculating a contact area $A_c$ from the actual indentation depth, and measuring hardness $H_{IT}$ of the material from the contact area, thus generating a stress-free curve (stress reference curve) for the reference specimen; repeatedly applying and removing an indentation load to and from an actual specimen of the material in a stressed state, thus generating a stressed curve for the actual specimen; and measuring the residual stress of the material using both a load difference $\Delta L$ obtained from comparison between the stress reference curve and the stressed curve and a contact area $A_s$ in a stressed state obtained from a loading curve.

The analysis of the indentation load-depth curve may comprise: when the material is a base metal exclusive of a weldment, adapting a second-order equation expressed as $L=K_b^o(h+\Delta h_a)^2$ to the analysis, wherein the subscript 0 means a stress-free state, the superscript b means the base metal, and $k_b^o$ is a slope of a loading curve in a stress-free curve (stress reference curve) of the base metal, and $\Delta h_a$ is an indenter tip compensation constant, which is a geometrical factor expressing an indenter tip that is not an ideally sharp tip, that is, has become blunt, and so $\Delta h_a$ means a difference between an indentation depth when an ideally sharp tip is used and an indentation depth when an actual indenter tip is used; and the step of measuring the maximum load and the maximum indentation depth comprises: finding a point of an actual maximum load ($L_{max}$) at each loading step in the indentation load-depth curve, and a point of an actual maximum indentation depth ($h_{max}$) at each unloading step in the indentation load-depth curve.

The analysis of the multiple loading curve may comprise: when the material is a weldment, adapting a second-order equation expressed as $L=K_w^o(h+\Delta h_a)^2$ to the analysis, wherein the subscript 0 means a stress-free state, the superscript w means the weldment, and $k_{0w}$ is a slope of a loading curve in a stress-free curve (stress reference curve) of the weldment, and the step of measuring the maximum load and the maximum indentation depth may comprise: finding a point of an actual maximum load $L_{max}$ at each loading step in the multiple loading curve, and a point of an actual maximum indentation depth $h_{max}$ at each unloading step in the multiple loading curve.

In the above-mentioned equation, $k_w^o$ is expressed as the equation $$k_w^o = \frac{H_{IT,o}^w}{H_{IT,o}^b} k_b^0 = \frac{\sigma_{IT}^W}{\sigma_{IT}^b} k_b^o,$$

wherein $k_b^0$ is a slope of a loading curve in a stress reference curve (stress-free curve) of a base metal, $H_{IT,0}^b$ and $H_{IT,0}^w$ are hardness of the base and hardness of the weldment, respectively, and $\sigma^b_{IT}$ and $\sigma^w_{IT}$ are strengths of the base metal and the weldment, respectively.

The strength of each of the base metal and the weldment may be a yield strength $\sigma_{IT,YS}$, a tensile strength $\sigma_{IT,UTS}$, an average strength $\sigma_{IT,f}$, or an indentation strength $\sigma_{IT,r}$.

The average strength $\sigma_{IT,f}$ may be an arithmetic average of the yield strength $\sigma_{IT,YS}$ and the tensile strength $\sigma_{IT,UTS}$, and the indentation strength $\sigma_{IT,r}$ may be a strength value corresponding to a modulus of strain, which is 0.08, in an indentation flow curve obtained through KS B 0950.

In the equation, $\Delta h_a$ is an indenter tip compensation constant, which is a geometrical factor expressing an indenter tip that is not an ideally sharp tip, that is, has become blunt, and so $\Delta h_a$ means a difference between an indentation depth when an ideally sharp tip is used and an indentation depth when an actual indenter tip is used.

The step of calculating the actual indentation depth $h_c$ from the maximum indentation depth may comprise: adapting an equation expressed as $h_c = f(h_{max} + \Delta h_a)$ to the calculation, wherein $h_c$ is the actual contact (indentation) depth, and f is a compensation constant of a ratio of the actual contact (indentation) depth to the maximum indentation depth $h_{max}$ measured using a sensor.

The compensation constant f is a ratio of the actual indentation depth $h_c$ to the maximum indentation depth $h_{max}$ measured using the sensor, and is expressed as an equation $$f = \frac{h_c}{h_{max} + \Delta h_a},$$

and in practice, due to pile-up or sink-in of the material, a part of a surface of the material, with which the indenter tip is in contact, is raised or depressed, so that the actual indentation depth $h_c$ varies, and so the compensation constant f to compensate for the variation is expressed as an equation $$f = 1.2445(1 - 0.6n)\left(1 - 7.2\frac{\sigma_{IT,YS}}{E_r}\right),$$

wherein the compensation constant f ranges from 0.94 to 1.12.

The step of calculating the actual contact area $A_c$ from the actual contact (indentation) depth $h_c$ may use an equation $$A_C = 24.5 h_C^2,$$

wherein $h_c$ is the actual contact (indentation) depth.

The step of calculating the indentation hardness $H_{IT}$ from the actual contact area $A_c$ may use an equation $$H_{IT} = \frac{L_{max}}{A_C},$$

wherein $L_{max}$ is the actual maximum load in each loading step and $A_c$ is the actual contact area.

The step of generating the stressed curve for the actual specimen of the material in a stressed state through the continuous indentation test may comprise: calculating the actual maximum load $L_{max}$ at each loading step and the maximum indentation depth $h_{max}$ that is the maximum depth at each unloading step in the continuous indentation test for the actual specimen, and calculating slopes $k_s^b$, $k_s^w$ of the loading curve in a stressed state from the loading curve.

The load difference may be a difference between a load $L^T$ or $L^c$ applied at a maximum indentation depth in the stressed curve (a slope of the loading curve in a stressed state) and a load $L^0$ applied at the same maximum indentation depth in the stress-free curve (a slope of the loading curve in a stress-free state), and the contact area is calculated using an equation $$A_s^T = \frac{L_s^T}{H_{IT}} \text{ or } A_s^C = \frac{L_s^C}{H_{IT}},$$

wherein $A^T_S$ and $A^C_S$ are contact areas in a stressed state (tensile stressed state, compressive stressed state), and $H_{IT}$ is the indentation hardness.

The residual stress of the base of the material may be expressed as an equation $$\sigma_{res} = \eta_1 \frac{\Delta L}{A_s},$$

wherein $\sigma_{res}$ is the residual stress, $\Delta L$ is a normal load difference induced from the stress-free curve and the stressed curve, $A_s$ is the contact area in a stressed state, and $\eta_1$ is a proportional constant to determine isotropic residual stress.

The residual stress of the weldment may be expressed as an equation $$\sigma_{res} = \eta_2 \frac{\Delta L}{A_s},$$

wherein $\sigma_{res}$ is the residual stress, $\Delta L$ is a normal load difference induced from the stress-free curve and the stressed curve, $A_s$ is the contact area in the stressed state, and $\eta_2$ is a proportional constant to determine anisotropic residual stress.

[Mode for Invention]

Herein below, preferred embodiments of the present invention will be described with reference to the accompanying drawings.

Figure 2:
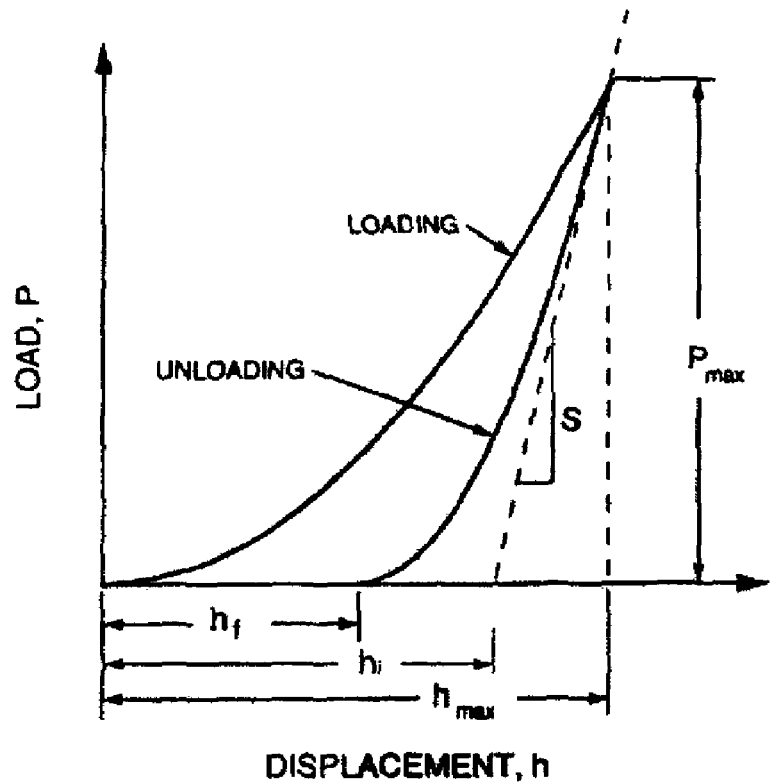
FIG. 2 is a graph of an indentation load-depth curve obtained using a residual stress measuring apparatus of the present invention.

FIG. 2 is a graph of indentation load-depth curves obtained using the residual stress measuring apparatus of the present invention.

As illustrated in FIG. 2, the actual indentation depth $h_c$ is calculated by defining the point of a maximum indentation depth $h_{max}$, which has a maximum depth, in an unloading curve section in the graph obtained from the indentation of a material. The actual indentation depth that is actually measured is defined by a ratio f of an indenter tip compensation constant $\Delta h_a$, which is a factor compensating for the indentation depth, to an indentation depth compensation constant.

However, unlike an ideal curve, in a practical test, the time of loading and the time of generating the maximum depth do not occur simultaneously.

Figure 3:
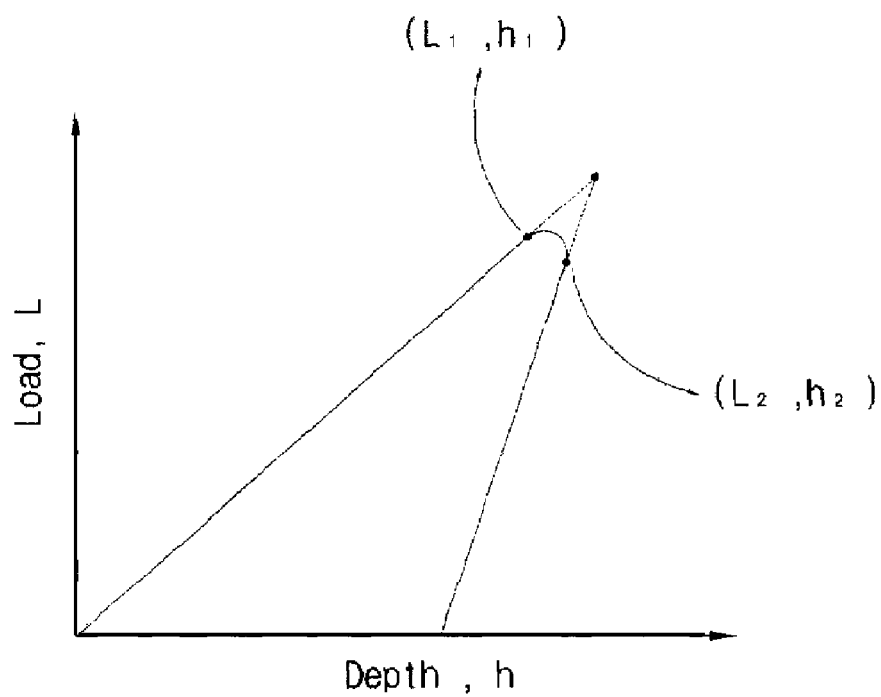
FIG. 3 is a graph illustrating the shape of an actual curve at the time of conversion from loading to unloading.

FIG. 3 is a graph illustrating the shape of an actual curve at the time of conversion from loading to unloading. In a conventional method of measuring residual stress, the maximum displacement point $h_{max}$ and maximum load $L_{max}$ are set to $L_2$ and $h_2$, respectively. In other words, the load at the time of generating the maximum depth is set to the maximum load prior to calculation.

To calculate the indentation depth from the unloading curve, the slope S of the unloading curve must be obtained. Furthermore, a contact area $A_c$ must be induced from both the maximum indentation depth $h_{max}$ and the slope S of the unloading curve. However, the calculation sensitively accounts for influences caused by an abnormal curve or data scattering which may be generated during an indentation test, so that there may be an error in the calculation.

Furthermore, to measure residual stress from the graph having the indentation load-displacement curve without separately calculating the slope and the unloading curve, it is required to simplify variables. To achieve the above-mentioned object, an operation is executed with the maximum load set to $L_1$ and the maximum depth set to $h_2$. In other words, after the point of the maximum load and the point of the maximum depth are checked, the load at the maximum load point is set to the maximum load and the depth at the maximum depth point is set to the maximum depth.

As described above, unlike the conventional method, in the method of the present invention, the maximum load is changed from $L_2$ to $L_1$, so that the hardness $H_{IT}$ increases and the residual stress is overestimated. However, due to the application of actual load, the present invention emphasizes the objective side of the measurement. Furthermore, the increase in hardness is negligible, so that the present invention precisely measures actual residual stress.

FIG. 5 is a sectional view of a material deformed by an ideally sharp tip, and FIG. 6 is a sectional view of a material deformed by a blunted tip. In an ideal indentation test of FIG. 10, the actual indentation depth may be 7d. However, due to elastic deformation of the indenter tip caused by repeated indentation as shown in FIG. 11, or pile-up or sink-in of a material, the actual indentation test is different from the ideal indentation test, so that error occurs in the actual indentation test.

The present invention uses a residual stress measuring apparatus that repeatedly loads and unloads a material and measures residual stress of the material. The residual stress measuring apparatus used in the present invention may be an apparatus disclosed in Korean Patent Registration No. 0416723, which was filed by and issued to the applicant of the present invention and entitled "Apparatus for Measuring Residual Stress, Methods of Measuring Residual Stress and Residual Stress Data Using the Apparatus, and Recording Medium for Storing Software for the Residual Stress Measuring Method".

To measure the residual stress of a material by continuously measuring variation in the indentation load applied to the material and variation in the indentation depth, an indentation load-indentation depth curve in a residual stressed state and an indentation load-indentation depth curve in a stress-free state are required, because it is necessary to compare the above-mentioned curves with an indentation load-depth curve of an actual specimen to be actually measured. The process of measuring residual stress of a material by inducing an indentation load-depth in a stress-free state will be executed as follows.

First, an object weldment for measurement of residual stress and a base metal of a specimen, which is exclusive of the weldment and is recognized as being in a stress-free state, are subjected to continuous indentation tests using a Vickers indenter and a spherical indenter, so that indentation load-depth curves are obtained. The residual stress measurement for the weldment will be described separately in the second embodiment.

The indentation load-depth curve obtained using the Vickers indenter is used for determination of the amount of load variation and contact area. The indentation load-depth curve obtained using the spherical indenter is used for the determination of indentation tensile properties of a material through KS B 0950.

The indentation load-depth curve obtained using the spherical indenter is used to induce a stress-free reference curve in a residual stress-free state of a weldment specimen, but is not required in the measurement of residual stress of the specimen exclusive of the weldment. Furthermore, the specimen limited to the weldment is a specimen, in which an actual junction having a biaxial anisotropic residual stress is formed, or a specimen having a voluntarily different or deviating stress distribution. However, residual stress of a material having an isotropic or uniaxial stress distribution may be measured through the same manner as disclosed in the above-mentioned Korean patent entitled "Apparatus for Measuring Residual Stress, Methods of Measuring Residual Stress and Residual Stress Data Using the Apparatus, and Recording Medium for Storing Software for the Residual Stress Measuring Method".

Figure 7:
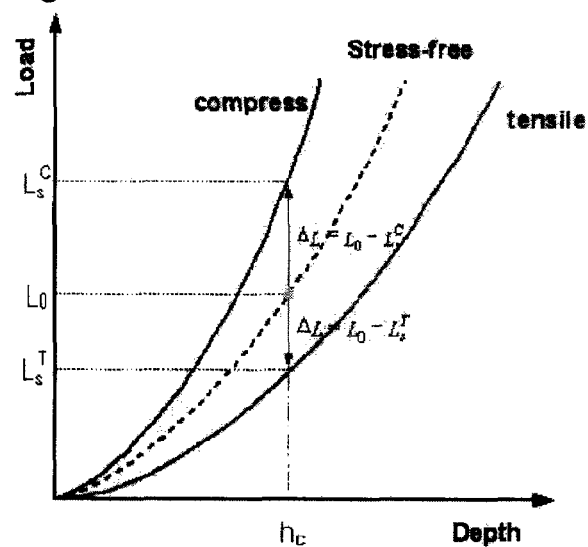
FIG. 7 is a graph illustrating the indentation load-depth curves respectively in a stress-free state and in a residual stressed state.

The method of measuring residual stress according to the present invention will be briefly described as follows. If isotropic tensile or compressive residual stress is parallel to the specimen surface, the slope of the indentation loading curve varies as shown in FIG. 7. To reach the maximum indentation depth, the specimen having tensile residual stress requires an indentation load that is lower than the load required in a stress-free state. However, the specimen having compressive residual stress requires an indentation load which is higher than the load required in a stress-free state. The increase or decrease in the indentation load is caused by residual stress. In other words, in the specimen having tensile residual stress, a normal load, which is induced by residual stress that is parallel to the surface of the specimen, is added to an externally applied load, so that the maximum indentation depth corresponding to the load lower than the load in a stress-free state can be obtained.

However, in a material having compressive residual stress, the normal load induced by the residual stress acts in a direction opposite the direction of the externally applied load, so that, to reach a predetermined maximum indentation depth, a higher load must be applied. Thus, residual stress of a material may be quantitatively measured by the analysis of residual stress-induced normal load which was defined through the comparison of indentation loading curves in a stress-free state and a residual stressed state measured through a continuous indentation test.

In other words, a reference specimen (stress-free state) is subjected to multiple continuous indentation tests using the above-mentioned residual stress measuring apparatus, so that curves are obtained from the multiple continuous indentation tests. Thereafter, a fitted equation of a loading curve and an actual indentation depth $h_c$ are obtained based on the curves obtained from the tests.

Only a loading curve is separated from the obtained indentation load-depth curve to execute a fitting process. This fitting process is required in order to accurately measure a value, because the shape of the unloading curve is distorted in the case of actual multiple indentations and so the curve is different from that of an actually applied load.

The loading curve in the indentation load-indentation depth curve obtained using a Vickers indenter for a base metal in a stress-free state will be expressed as follows.

Figure 8:
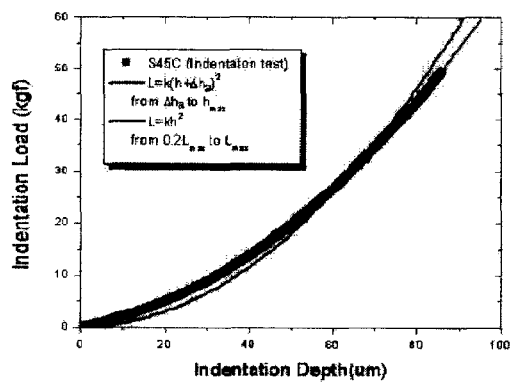
FIG. 8 is a graph illustrating an indentation load-depth curve which was fitted into a second-order equation.

The load applied when Vickers indentation tests, indicating a certain hardness, are executed is proportional to an indentation area, so that the relationship between the indentation load and indentation depth at the time of loading can be fitted in the form of a second-order equation which is proportional to the slope k of a loading section ($L=kh^2$). However, the curve obtained using an indenter tip that is not ideally sharp is different from an actual indentation curve. Thus, the relationship between the indentation load and indentation depth at the time of loading is fitted in the form of a modified second-order equation, as expressed in Equation 7, by adapting $\Delta h_a$, which expresses the extent of bluntness of the indenter tip, thus obtaining an experimental equation. When the modified second-order equation, in which modified $\Delta h_a$ is adapted, is compared to the original second-order equation ($L=kh^2$) as shown in FIG. 8, it is noted that the shape of the modified second-order equation agrees with an actual indentation curve.

$$L=k(h+\Delta h_a)^2 \quad \text{[Equation 7]}$$

wherein k is a coefficient of the equation expressing the relationship between the indentation load and the indentation depth, and $\Delta h_a$ means an indentation depth to compensate for the initial section in the loading curve.

Furthermore, the loading curve of the indentation load-depth curve obtained using a Vickers indenter for both the base metal (stress-free state) and the weldment (stress-free state) can be expressed as Equation 8 using Equation 7. However, in the case of a weldment in a stressed state, it is very difficult to measure the stress-free state from the indentation load-depth curve without using a mechanical or thermal technique. Thus, a stress-free reference curve in a stress-free state is estimated using a strength ratio obtained from indentation tensile properties (KS B 0950).

a) Base Metal (stress-free state): $L=K_b^o(h+\Delta h_a)^2$ b) Weldment (stress-free state): $L=K_w^o(h+\Delta h_a)^2$     [Equation 8]

wherein the subscript 0 means a stress-free state, and superscripts b and w mean the base metal and the weldment, respectively. Furthermore, the weldment means that it includes a weld metal and a thermally affected part, and the stress-free state means that no residual stress is present. The following first embodiment executes a process of measuring both the maximum load and the maximum indentation depth from the loading-unloading curve, calculating measuring an actual indentation depth and a contact area, measuring a normal load difference induced from the actual indentation depth, and measuring the residual stress of the material.

FIRST EMBODIMENT

Measurement of Residual Stress of a Material Exclusive of a Weldment

The method of measuring residual stress of a material exclusive of a weldment is a technique of measuring the residual stress of the material from a normal load difference $\Delta L$, which is conducted through comparison of a reference specimen (stress-free state) and an indentation load-depth curve obtained in a stressed state, and taken from the slope of a curve generated depending on an actual indentation depth $h_c$, contact area $A_c$, indentation hardness $H_{IT}$ and residual stress. The residual stress measuring method includes steps of: obtaining a stress reference curve in a stress-free state, obtaining a stressed curve in a stressed state, comparing the two curves respectively obtained in the stress-free state and stressed state to each other, and measuring the residual stress of the material using both a load difference $\Delta L$ between the two curves obtained through the comparison and a contact area obtained from the loading curve.

To obtain the stress reference curve (stress-free curve) and the stressed curve, respective indentation load-displacement curves at a point of the stress-free state and a point of the stressed state must be provided.

Thus, it is required to execute the steps of: obtaining an indentation load-depth curve in a stress-free state by analyzing the obtained multiple loading curve, measuring both the maximum load and the maximum indentation depth from the indentation load-depth curve, calculating an actual indentation depth $h_c$ from the maximum indentation depth, calculating a contact area $A_c$ from the actual indentation depth, and measuring the hardness $H_{IT}$ of the material from the contact area. (refer to "Indentation Hardness Measured Through Capsuled Indentation Tests" (ISO 14577-1))

The step of analyzing the loading curve measured from the indentation load-depth curve in a stress-free state can be executed using the part a of Equation 8. The step of measuring the maximum load and the maximum indentation depth comprises: defining both the point of the actual maximum load at each loading step and the point of the maximum indentation depth $h_{max}$ which has the maximum displacement, in an unloading curve obtained from the actual multiple indentation load-depth curve (curve expressing the repetition of loading-holding-unloading-holding)

Thereafter, the step of calculating the actual indentation depth using the maximum indentation depth is executed using Equation 9

$$h_c=f(h_{max}+\Delta h_a) \quad \text{[Equation 9]}$$

wherein $h_c$ is an actual indentation depth, f is a compensation constant of a ratio of an actual contact (indentation) depth to the maximum indentation depth $h_{max}$ measured using a sensor, $h_{max}$ is the maximum indentation depth, and $\Delta h_a$ is an indenter tip compensation constant.

$\Delta h_a$ is not the indentation depth of an actual material, but is a geometrical factor expressing the extent of bluntness of the indenter tip. To avoid confusion between this variable $\Delta h_a$ and other variables, a subscript a is used in $\Delta h_a$. In view of the geometrical relationship of sharpness of an indenter tip, the variable $\Delta h_a$ is required for calculation of the actual indentation depth in the capsuled indentation test (referred to ISO 14577-1). Furthermore, $\Delta h_a$ means a difference (a correction depth for tip bluntness) between the actual contact (indentation) depth $h_c$ measured using the ideally sharp tip and an indentation depth $h_b$ measured using the blunted tip as shown in FIGS. 5 and 6, and means a factor compensating for the actually measured contact (indentation) depth $h_c$.

The compensation constant f (the ratio of the actual contact depth to the maximum depth) is used to compensate for the variable actual indentation depth $h_c$. Due to pile-in or sink-in of actual material, a part of the material surface which is in contact with the indenter tip may be raised or depressed, so that the actual indentation depth ($h_c$) varies, and so the compensation constant f is used to compensate for the variation. The compensation constant f, which is the ratio of the actual indentation depth $h_c$ to the maximum indentation depth $h_{max}$ measured by a sensor and ranges from 0.94 to 1.12, is illustrated in FIG. 4.

The compensation constant f in the case of using an ideally sharp tip as illustrated in FIG. 5 will be expressed as the Equation 10.

$$f = \frac{h_c}{h_{\max}} \quad \text{[Equation 10]}$$

(The compensation constant f means a ratio of an actual indentation depth to a maximum indentation depth in the case of using an ideally sharp tip)

The actual indentation depth $h_c$ may be expressed as a multiplication of the compensation constant f by the maximum indentation depth $h_{max}$. In the equation, the compensation constant f is a compensation constant which is defined in consideration of pile-up and sink-in of a material, which causes accumulation or entry of the material at positions around the corners of an indentation mark during indentation of the material. It is possible to determine an indentation depth corresponding to the maximum load at each step in the multiple indentation load-depth curve by using Equation 14 in Equation 15.

$L_{max}=24.5Hf^2h_{max}^2$ a) ideally sharp tip $L_{max}=24.5Hf^2(h_{max}+\Delta h_a)^2$ b) blunted tip  [Equation 11]

However, in the case of a blunted tip, it is required to consider the difference $\Delta h_a$ between the maximum indentation depth $h_{max}$ measured using the sensor and the indentation depth caused by the blunted tip. This is expressed as Equation 12 (see FIG. 6)

$$f = \frac{h_c}{h_{\max} + \Delta h_a} : \text{ratio of the actual} \quad \text{[Equation 12]}$$

indentation depth to the maximum indentation depth in consideration of blunted tip The compensation constant f was determined through tests for a variety of materials and may be expressed as Equation 13.

$$f = 1.2445(1 - 0.6n)\left(1 - 7.2\frac{\sigma_{IT,YS}}{E_r}\right) \quad \text{[Equation 13]}$$

wherein $\sigma_{IT,YS}$ means a yield strength, and $E_r$ is a reduced modulus of elasticity, which is the same as that disclosed in Korean Patent Application No. 2004-91031, filed by the applicant of the present invention on Nov. 9, 2004 and entitled "Method of Measuring Fracture Toughness Using a Continuous Indentation Technique".

Through the continuous indentation tests for a variety of materials, the compensation constant can be obtained using Equation 13. Furthermore, actual compensation constant values obtained through actual tests are given in the Table of FIG. 4.

As shown in FIG. 4, the compensation constant values obtained using the variety of material range from 0.94 to 1.12, and the average value of the compensation constant values is 1.04, so that, in the following description, the actual indentation depth will be calculated using the compensation constant f set to 1.04. However, it should be understood that the compensation constant may vary depending on the property of a material or the procedure test.

The step of calculating a contact area using the actual indentation depth will be executed using Equation 14

$$A_c = 24.5h_c^2 \quad \text{[Equation 14]}$$

wherein the contact area $A_c$ is calculated using the actual indentation depth $h_c$ obtained from Equation 9, and Equation 14 is induced as a geometric number determined in consideration of the shape of a Vickers indenter tip. (indentation hardness measured through capsuled indentation test (referred to ISO 14577-1))

The step of calculating the indentation hardness using the contact area is executed using Equation 15.

$$H_{IT} = \frac{L_{\max}}{A_C} \quad \text{[Equation 15]}$$

wherein $H_{IT}$ means the indentation hardness (ISO 14577-1) obtained from a capsuled indentation test, and $L_{max}$ is the maximum load at each step in the multiple indentation load-depth curve.

It is required to calculate a stress-free reference curve in a stress-free state and, thereafter, calculate a stressed curve in a stressed state. Once the tests for the reference specimen (stress-free state) have been finished, tests for a specimen to measure residual stress are executed. In the above case, because the intrinsic hardness does not vary with residual stress within the limits of elasticity, it is possible to reduce a contact depth corresponding to an indentation load by using a contact depth $h_c$ obtained for the reference specimen. Thus, it is not necessary to execute a partial unloading step in the above case.

After executing the indentation test to secure the stressed curve in a stressed state, the loading curve is subjected to a fitting procedure in the same manner as that described for the previous step of obtaining the stress-free reference curve in a stress-free state. In the step of measuring both the maximum load and the maximum indentation depth, a point of the actual maximum load $L_{max}$ is defined in each loading curve and a point of the maximum indentation depth $h_{max}$, which has the maximum depth, is defined in each unloading curve in the actual multiple indentation load-depth (indentation depth) curve (curve expressing the repetition of loading-holding-unloading-holding). The loading curve is analyzed using the parts a and b of Equation 8, thus inducing the slopes $k_s^b$ and $k_s^w$ of the loading curve in a stressed state.

Thereafter, the curves obtained in a stress-free state are compared to the curves in a stressed state. As illustrated in FIG. 7, a normal load difference $\Delta L$ is measured such that the difference $\Delta L$ is induced from the curves obtained in the stress-free state and stressed state at the actual contact (indentation) depth $h_c$ measured from the reference curve in a stress-free state. Furthermore, it is possible to indirectly deduce the contact area in a residual stressed state using Equation 16, which expresses that the intrinsic hardness is constant regardless of the type of residual stress (tensile or compressive residual stress).

$$H = \frac{L_s^T}{A_s^T} = \frac{L_0}{A_c} = \frac{L_s^C}{A_s^C} \quad \text{[Equation 16]}$$

wherein the intrinsic hardness H is equal to the indentation hardness $H_{IT}$ measured through the indentation test, and the subscripts 0 (zero) and S mean a stress-free state and a stressed state, respectively. $A_c$ means the contact area in a stress-free state, while $A_s$ means an actual contact area. Furthermore, the superscripts T and C mean tensile stress and compressive stress, respectively. $L_0$ means the maximum load $L_{max}$ in a stress-free state. (reference documents: T. Y. Tsui, W. C. Oliver and G. M. Pharr; J. Mater. Res., 11 (1996) 752)

Figure 9:
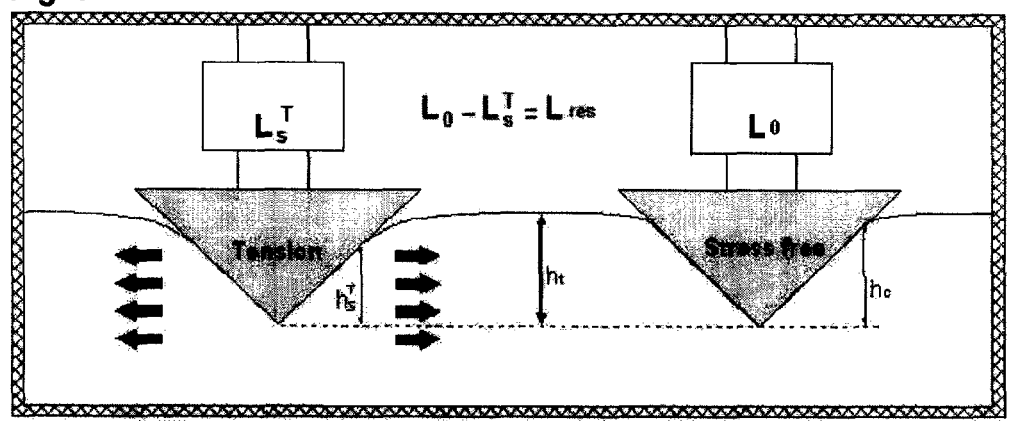
FIG. 9 is a sectional view illustrating a difference between contact states of an indenter tip relative to a specimen in a tensile stressed state and in a stress-free state.

FIG. 9 illustrates the modeling of contact shapes of indenter tips relative to specimens according to residual stress during depth-controlled relaxation, wherein indentation is executed such that the maximum indentation depth maintains constant. When an indentation test is executed such that the maximum indentation depth is maintained constant, the indentation load applied by tensile stress decreases in comparison with the indentation load measured in the stress-free state. Furthermore, to maintain the indentation hardness constant, the contact area is linearly proportional to the indentation load. In other words, as the tensile stressed state is changed to the stress-free state, the externally applied load to reach the maximum indentation depth increases from $L_s^T$ to $L_0$. Furthermore, to maintain the constant indentation hardness $H_{IT}$, the contact depth increases from $h_s^T$ to $h_c$ in the same manner as that described for the increase in the applied load. In addition, the contact area, which varies depending on the contact depth, increases from $A_s^T$ to $A_c$. Thus, it is noted that the intrinsic hardness in a stress-free state and the intrinsic hardness in a tensile stressed state are constant.

From Equation 16, which expresses that the intrinsic hardness is constant regardless of the type of residual stress, the contact area in the stressed curve can be indirectly deduced using Equation 17.

$$A_s^{T,C} = \frac{L_s^{T,C}}{H} \quad \text{[Equation 17]}$$

wherein the subscript s means a stressed state, and the superscripts T and C mean tensile stress and compressive stress, respectively.

$L_s^{T,C}$ is a normal load induced from a stressed curve in a stressed state (tensile or compressive stressed state) at the maximum indentation depth, and $H_{IT}$ means the indentation hardness induced through Equation 15. Thus, the contact area in a stressed curve can be induced from both the induced normal load and the indentation hardness measured in the stress-free state.

The step of measuring the residual stress of the material using the contact area $A_s$ measured from the stressed curve in the stressed state, the stress-free curve (stress reference curve) induced from the measured actual contact (indentation) depth, and the stressed curve load difference $\Delta L$ is executed using Equation 18.

$$\sigma_{res} = \eta_1 \frac{\Delta L}{A_s} \quad \text{[Equation 18]}$$

wherein $\sigma_{res}$ is the residual stress, $\Delta L$ is the normal load difference induced from the stress-free curve and the stressed curve, $A_s$ is the contact area in a stressed state, and $\eta_1$ is a proportional constant to determine isotropic uniaxial or biaxial residual stress. The proportional constant $\eta_1$ is defined as follows.

When uniaxial residual stress ($\sigma_{res,x} \neq 0$, $\sigma_{res,y} = \sigma_{res,z} = 0$) and isotropic biaxial residual stress ($\sigma_{res,x} = \sigma_{res,y} \neq 0$, $\sigma_{res,z} = 0$) are applied to the surface of a material, the residual stress can be measured using the method expressed as Equation 18. (the proportional constant $\eta_1$ is defined as a constant $\alpha$ in the above-mentioned Korean Patent entitled "Apparatus for Measuring Residual Stress, Methods of Measuring Residual Stress and Residual Stress Data Using the Apparatus, and Recording Medium for Storing Software for the Residual Stress Measuring Method")

To define the residual stress inducing normal load using only a deviator stress component having a direct relationship with plastic deformation, the reaction between the indentation deformation and the residual stress is analyzed. The indentation deformation, caused by a rigid tip, is modeled as a sectional shape, in which the small region enlarged in the form of a shell surrounds an incompressible core. Furthermore, the hydrostatic stress in a cavity, which leads the Tresca yield criterion to the boundary between the cavity and elastic section and induces initial yield, is set to $-2\sigma y/3$. If the material has an elastic-rigid plastic behavior, the plastic region in the outside of the cavity corresponding to the increase in the hydrostatic stress gradually increases. In the above case, the stress distribution in the plastic region is analyzed in combination with the stress analysis and yield conditions for ball shells. Furthermore, in a complex indentation deformation stress field, it is considered that the stress $-2\sigma y/3$ in a core is overlapped with externally applied isotropic biaxial residual stress, $\sigma_{res}(=\sigma_{res,x}=\sigma_{res,y})$.

If isotropic biaxial residual stress is applied to a core, the hydrostatic stress in the cavity varies to collaterally generate a shearing stress component. In Equation 19, the sum $\sigma_{com}$ the hydrostatic stress in the core and the isotropic biaxial residual stress may be decomposed into hydrostatic stress and deviator stress. In the above case, the hydrostatic stress has no relationship with the plastic deformation of the material, so that influence of the indentation deformation caused by residual stress can be verified from the deviator stress component. In the deviator stress components of Equation 19, the residual stress, which influences the indentation load perpendicular to the thin film surface, is verified as $-2\sigma y/3$ in $\sigma z$.

Further, the above-mentioned measured stress defines that the ratio of average contact pressure Pm, which results from division of the indentation load by the contact area in the indentation test, to genuine stress is constant throughout an entire plastic region. Thus, Equation 20 can be provided. In Equation 20, the average contact pressure Pm becomes a general predictor of stress determined using an indentation test, and to reduce average contact pressure to the general predictor of genuine stress of a general material, a plastic constraint factor $\Psi$ of the material is used.

An indentation load is applied to a specimen having isotropic biaxial tensile residual stress, thus forming a maximum indentation depth. Thereafter, the tensile residual stress is relaxed to cause an increase in the indentation load. Thereafter, from Equations 19 and 20, the amount of increase in the applied load expressed as Equation 21 is newly defined as a residual stress inducing normal load. In other words, if the indentation test is controlled to maintain the maximum indentation depth constant, an indentation load difference, which is equal to a value of the residual stress inducing normal load, is generated by residual stress.

$$\sigma_{com} = \begin{pmatrix} \frac{-2}{3}\sigma_y & 0 & 0 \\ 0 & \frac{-2}{3}\sigma_y & 0 \\ 0 & 0 & \frac{-2}{3}\sigma_y \end{pmatrix} + \begin{pmatrix} \sigma_{res} & 0 & 0 \\ 0 & \sigma_{res} & 0 \\ 0 & 0 & 0 \end{pmatrix} =$$ [Equation 19]

$$\begin{pmatrix} \frac{-2}{3}(\sigma_y - \sigma_{res}) & 0 & 0 \\ 0 & \frac{-2}{3}(\sigma_y - \sigma_{res}) & 0 \\ 0 & 0 & \frac{-2}{3}(\sigma_y - \sigma_{res}) \end{pmatrix} +$$

$$\begin{pmatrix} \frac{1}{3}\sigma_{res} & 0 & 0 \\ 0 & \frac{1}{3}\sigma_{res} & 0 \\ 0 & 0 & \frac{-2}{3}\sigma_{res} \end{pmatrix}$$

$$\sigma = \frac{P_m}{\Psi} = \frac{1}{\Psi} \cdot \frac{L}{A}$$ [Equation 20]

$$\frac{1}{\Psi}\frac{\Delta L}{A_s} = \frac{2}{3}\sigma_{res}$$ [Equation 21]

wherein $\Psi$ is a plastic constraint factor, which means a ratio of average contact pressure to genuine stress in an ideal plastic region, and is set to 3.0 in the case of metals. (D. Tabor; "*The Hardness of Metals*" Clarendon Press, Oxford, UK (1951))

If both sides of Equation 21 are modified using a residual stress variable $\sigma_{res}$ in the same manner as that for Equation 18, the proportional constant $\eta_1$ to determine isotropic biaxial residual stress can be defined as expressed in Equation 22.

$$\eta_1 = \frac{1}{\Psi}\frac{3}{2} = \frac{1}{2}$$ [Equation 22]

Figure 10:
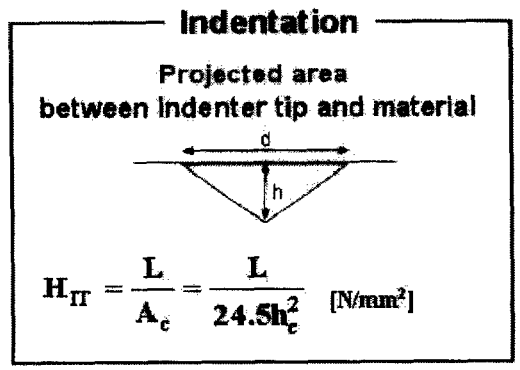
FIG. 10 is a view schematically illustrating a technique of measuring indentation hardness $H_{IT}$ in the case of an ideally sharp tip.
Figure 11:
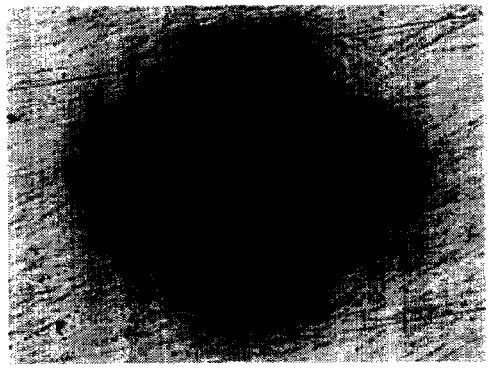
FIG. 11 is a sectional view illustrating an actual contact state of an indenter tip relative to a material.

FIG. 9 is a sectional view illustrating the difference between contact states of a tip relative to a specimen in a tensile stressed state and a stress-free state, and FIG. 10 is a view schematically illustrating a technique of measuring indentation hardness $H_{IT}$ in the case of an ideally sharp tip. FIG. 11 is a sectional view illustrating an actual contact state of a tip relative to a material. As shown in FIGS. 10 and 11, in a continuous indentation process in which a tip comes into repeated contact with the surface of a material, there may occur a difference between the maximum indentation depths due to pile-up and sink-in of the material surface. Such a difference between the maximum indentation depths can be viewed with the naked eye. Furthermore, an error may occur during the measurement by a blunted tip.

In the above case, $\Delta h_a$ means the amount of reduced length of the tip when the tip becomes blunted due to repeated indentation tests. (see FIG. 6)

Through the above-mentioned process, it is possible to measure residual stress of a material using a continuous indentation test.

SECOND EMBODIMENT

Measurement of Residual Stress for a Weldment

The biggest problem experienced in the conventional method of measuring residual stress of a weldment resides in that the weldment in a residual stress-free state cannot be measured in the field. Because a material actually used in the field cannot be directly subjected to a mechanical or thermal technique to remove stress, it is not easy to quantitatively measure residual stress of the material. Therefore, to remove stress, a destructive technique must be used. However, the destructive technique of removing stress from a material cannot be adapted to field use, but may only be used in laboratories. Furthermore, to adapt a conventional nondestructive technique to measure residual stress in the field, a physical method is used to approximate a residual stress-free state. However, the conventional nondestructive technique cannot reduce a measurement error caused both by its theoretical background and by data comparison, so that it has not been recognized as a quantitative measurement technique.

Figure 12:
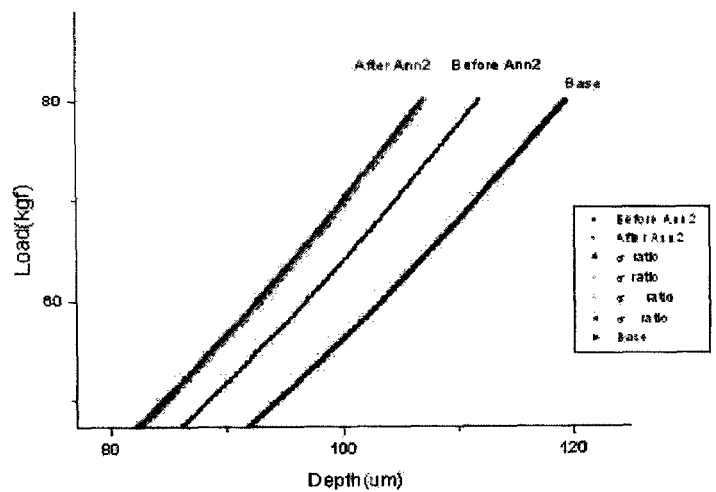
FIG. 12 is a graph illustrating comparison of stress-free curves of API X65, which were respectively induced through annealing and using an indentation strength ratio.

However, the residual stress measuring method using the continuous indentation test technique according to the present invention does not use the physical method, which has been used in the conventional nondestructive measuring technique. The method of the present invention quantitatively measures residual stress using the continuous indentation test technique, which is a mechanical technique of repeatedly loading and unloading the surface of a material, and precisely estimates a reference curve in a residual stress-free state using a ratio of the weldment to the base metal as shown in FIGS. 12 and 13 (comparison of stress-free curve using annealing). Furthermore, the present invention is advantageous in that it measures residual stress from direct deformation behavior of a material by estimating a stress-free curve of a weldment without being affected externally.

Furthermore, the residual stress-free state of the weldment is induced from a base of the material, the fine structure of which is different from that of the weldment and which is remote from the weldment. If a predetermined load is applied to a material surface using a hard tip, an indentation mark is formed on the material surface by the indentation load. In the above case, it is possible to estimate indentation hardness $H_{IT}$, which is a strength property, from the applied indentation load and the size of the indentation mark. This is equal to that described for the first embodiment. The indentation hardness is in proportion to the slope k of a loading section ($L=kh^2$) of a curve of the applied indentation load L relative to the indentation depth h (indentation load-depth curve). Furthermore, the indentation hardness may also be expressed as the part b of Equation 8 by adapting the amount $\Delta h_a$, which is the difference caused by an unideal curve obtained from the degree of blunting of the tip, to the loading section. In other words, as the subject material has higher indentation hardness, the slope of the loading section of the indentation load-depth curve increases. Furthermore, using the concept that the above-mentioned theory and the indentation tensile properties have no relationship with residual stress, it is noted that the indentation hardness $H_{IT}$, the strength $\sigma_{IT}$ and the value k can be maintained at a constant ratio and are expressed as Equation 23.

$$\frac{K_w^o}{k_b^o} = \frac{H_{IT,o}^W}{H_{IT,o}^b} = \frac{\sigma_{IT}^w}{\sigma_{IT}^b}$$ [Equation 23]

$$k_w^o = \frac{H_{IT,o}^W}{H_{IT,o}^b} k_b^o = \frac{\sigma_{IT}^w}{\sigma_{IT}^b} k_b^o$$ [Equation 24]

1. In Equations 23 and 24, the superscripts w and b mean a weldment and a base, respectively.

2. In Equations 23 and 24, the subscript 0 (zero) means a stress-free state.

3. In Equations 23 and 24, the subscript IT means values obtained through the indentation.

In the above equations, $k^o_b$ and $k^o_w$, mean the slopes of the base metal and the weldment in a residual stress-free state, respectively, and $H^b_{IT,0}$, $H^w_{IT,0}$, $\sigma_{IT}^b$ and $\sigma_{IT}^w$ mean indentation hardness and strength of the base metal and the weldment in a residual stress-free state.

However, the indentation hardness in a residual stress-free state of the weldment may influence the indentation depth due to behavior of the material (pile-up or sink-in of the material) which may be formed around an indentation mark by residual stress, so that the indentation hardness cannot be directly measured in the field. Thus, to solve the above-mentioned limitation, first, it is assumed that strength is not influenced by residual stress within a rigid plastic region regardless of residual stress (Q1, Q2), and, thereafter, the stress-free reference curve of the weldment is estimated using Equation 24 and the theory expressing that the ratio of the indentation hardness $H_{IT}$ to the strength $\sigma_{IT}$ is constant. Furthermore, the above-mentioned theory can be verified from the following theses, and FIG. 14 shows that only the yield strength $\sigma_{IT,YS}$ is influenced by residual stress. (see FIG. 14)

1. Bart Goes, Javier Gil-Sevillano, Urbain D'Haene, Int. J. Mech. Sci. 41 (1999)

2. J. G. Swadener, B. Taljat, G. M. Pharr; J. Mater. Res. Vol. 16, No. 7 (2001)

To obtain $k^o_w$ based on the above-mentioned theory, the concept of strength, which is proportional to indentation hardness, $H_{IT}$, is used. The relationship between indentation hardness and strength is studied and verified using conventional equations, $HV=3*\sigma_{IT,UTS}$ and $HB=3*\sigma_{IT,YS}$. However, it is noted that the proportional constants C of a variety of material do not have the same value, but have slightly deviating values. This is because, if a material having a predetermined indentation hardness $H_{IT}$ is largely deformed within a range from a yield point to a maximum tensile strength point, or if the material has a large strain hardening range, it does not sufficiently account for the strength of the material using either the yield strength or the tensile strength. Thus, the concept of an average strength $\sigma_{IT,f}$ of the yield strength $\sigma_{IT,YS}$ and the tensile strength $\sigma_{IT,UTS}$, which can account for the two strengths, prevails. Furthermore, using a theory that the modulus of strain corresponding to a shearing strain occurring around the tip during a Vickers indentation test has a constant value 0.08, a strength $\sigma_{IT,r}$ corresponding to the constant modulus of strain is calculated. Thereafter, it is estimated that the ratio of calculated strength to hardness is constant, and verification of the estimation is executed (see FIG. 15). In other words, a verification test is executed using the one among variously defined strengths that has the smallest deviation in proportional constant relative to indentation hardness.

In the following description, the strength $\sigma_{IT}$ is simply expressed as $\sigma$, and the strengths may be classified into $\sigma_{YS}$, $\sigma_{UTS}$, $\sigma_f$ and $\sigma_r$.

If indentation hardness for each material is calculated and is, thereafter, divided by strength using an average proportional constant, a value which converges on 1 can be provided. In the above case, if the variety of material have values slightly deviating from the average proportional value, the value cannot converge on 1. FIG. 15 shows that the strengths having small deviation values are $\sigma_f$ and $\sigma_r$. Among the two strengths, $\sigma_f$ can be more effectively adapted on a job site, so that $\sigma_f$ is preferentially subjected to the test along with $\sigma_{YS}$, $\sigma_{UTS}$. In other words, to calculate $k^o_w$, the yield strength and tensile strength of the weldment and the base are determined through the indentation test and, thereafter, an average strength $\sigma_f$ of the two strengths is determined. Thereafter, the strength ratio of the weldment to the base metal is multiplied by $k^o_b$, thus determining $k^o_w$ as expressed as Equation 24. ($\sigma_r$ means an indentation strength corresponding to a modulus of strain 0.08 in an indentation flow curve obtained through KS B 0950)

In the tests, steel specimens API X65 and SS400 are used. After each specimen is cut, the cut specimens are welded to provide a weldment. Thereafter, strengths and indentation hardnesses of the weldment and the base metal of the specimen are determined through indentation tests. To verify $k^o_w$, which is determined by multiplying the ratios of $\sigma_f$, $\sigma_{YS}$ and $\sigma_{UTS}$ of the weldment to the base by $k^o_b$ of the base, a residual stress removing annealing process is executed prior to the comparison. During the annealing process, the two specimens are heated to 600° C. in a furnace and, thereafter, kept in the furnace for two hours prior to being cooled in the furnace.

From the tests, it is noted that the ratios of $\sigma_r$, $\sigma_f$, $\sigma_{YS}$, and $\sigma_{UTS}$ Of the steel specimens API X65 agree with each other as shown in FIG. 12. In the case of the steel specimen SS400, the ratios of $\sigma_r$ and $\sigma_f$ agree with each other although they deviate slightly from the annealing results shown in FIG. 13. Variation in a loading curve coefficient according to strength definition is given in Table 1.

TABLE 1

|  | post weld heat treatment (annealing) | σr | σf | σUTS | σYS |
| --- | --- | --- | --- | --- | --- |
| k°w (API X65) | 0.00697 | 0.00696 | 0.00697 | 0.00695 | 0.00700 |
| k°w (SS400) | 0.00510 | 0.00501 | 0.00497 | 0.00464 | 0.00553 |

From the above-mentioned tests, it is noted that, if the strength ratio of a weldment to the base of a material is used, a residual stress-free state required in the process of measuring residual stress of the weldment in the field can be induced without using a thermal or mechanical technique. Thus, a load difference ΔL induced by residual stress can be determined by comparison with the slope of a loading curve of a weldment in a residual stressed state.

In the same manner as that described for the step of measuring hardness of a base metal in the method of measuring residual stress of the base exclusive of the weldment, an indentation hardness $H_{IT}$ of the base metal is determined. Furthermore, a stress-free reference curve in a residual stress-free state is estimated by adapting Equation 24, which uses the determined indentation hardness and the strength ratios, to the part b of Equation 8.

Like the method of measuring "residual stress of a material exclusive of a weldment", the measurement of residual stress of the weldment comprises the steps of: generating a stress reference curve in a stress-free state; generating a stressed curve in a stressed state; comparing the curves generated in the stress-free state and the stressed state to each other; and measuring residual stress using a load difference $\Delta L$ between the two curves obtained from the comparison and a contact area obtained from a loading curve (see FIG. 7).

However, the technique used in the measurement of "residual stress of a material exclusive of a weldment" cannot be adapted to the measurement of residual stress of the weldment having an anisotropic stress structure. This is because residual stress is present in the weldment due to forcible constraining, quick heating and quick cooling. Thus, it is impossible to directly estimate a stress-free curve (stress reference curve) in a residual stress-free state of the weldment. Therefore, the slop $k_o^w$ of a stress-free reference curve of the weldment is first determined by adapting Equation 24, which is defined by the strengths of the base and the weldment, to the part b of Equation 8, prior to inducing a stress-free curve (stress reference curve) of the weldment.

To measure the strengths of the base and the weldment, tests are executed by changing an existing tip (Vickers tip) to another tip (spherical tip) in a residual stress measuring apparatus, thus generating an indentation load-depth curve. Thereafter, the indentation load-depth curve is analyzed through KS B 0950 to determine the properties of the base metal and the weldment.

Through the above-mentioned process, the stress-free curve in a stress-free state and the stressed curve in a stressed state can be determined. Thereafter, a load difference $\Delta L$ can be induced from an actual contact (indentation) depth. In the same manner as that described for the first embodiment, the measurement of indentation hardness of a material from both the actual contact (indentation) depth and the contact area comprises the steps of: analyzing a multiple loading curve determined to obtain an indentation load-depth curve in a stress-free state; measuring the maximum load and maximum indentation depth from the indentation load-depth curve; calculating an actual contact (indentation) depth $h_c$ from the maximum indentation depth; calculating a contact area $A_c$ from the actual contact (indentation) depth; and measuring hardness $H_{IT}$ of the material from the contact area.

Furthermore, the stressed curve is generated and analyzed in the same manner as that described for the first embodiment and, thereafter, an indentation load-depth curve is measured.

Thereafter, the step of comparing the curves measured in the stress-free state and the stressed state with each other is executed.

In other words, the contact area in a stressed state is determined using Equations 16 and 17, and the step of determining a normal load in a stress-free state and a stressed state induced from an actual contact depth is executed.

Like the measurement of residual stress of a material exclusive of a weldment, residual stress $\sigma_{res}$ of the weldment is induced. However, unlike the measurement of residual stress of a material exclusive of a weldment, anisotropic residual stress is applied to the weldment, so that the residual stress of the weldment is measured using another proportional constant $\eta_2$. In the above case, Equation 25 is used.

$$\sigma_{res} = \eta_2 \frac{\Delta L}{A_s} \quad \text{[Equation 25]}$$

wherein $\sigma_{res}$ is residual stress, $\Delta L$ is a normal load difference induced from the stress-free curve and the stressed curve, $A_s$ is a contact area in a stressed state, and $\eta_2$ is a proportional constant to determine anisotropic uniaxial or biaxial residual stress.

Furthermore, unlike the first embodiment, biaxial anisotropic residual stress is applied to the weldment of a steel material, so that it is necessary to consider the biaxial anisotropic residual stress present in the weldment.

Assuming that the maximum principal stress directional component of biaxial residual stress present in a steel weldment is $\sigma_{res,x}$ and the minimum principal stress directional component is $\sigma_{res,y}$ in view of absolute stress values, the residual stress can be expressed as $p\sigma_{res,x}$ using a stress-proportional constant p. In the above case, the stress-proportional constant p ranges from −1.0 to +1.0. If no normal residual stress, which is present in a direction perpendicular to a material surface (indentation test direction), is present in the weldment in the same manner as that described for the first embodiment, the residual stress of the weldment can be expressed as Equation 26, which is a matrix equation of deviator stress, which directly affects the hydrostatic stress and the plastic deformation, which are similar.

$$\begin{pmatrix} \sigma_{res,x} & 0 & 0 \\ 0 & \sigma_{res,y} & 0 \\ 0 & 0 & 0 \end{pmatrix} = \begin{pmatrix} \sigma_{res} & 0 & 0 \\ 0 & k\sigma_{res} & 0 \\ 0 & 0 & 0 \end{pmatrix} = \quad \text{[Equation 26]}$$

$$\begin{pmatrix} \frac{(1+k)\sigma_{res}}{3} & 0 & 0 \\ 0 & \frac{(1+k)\sigma_{res}}{3} & 0 \\ 0 & 0 & \frac{(1+k)\sigma_{res}}{3} \end{pmatrix} +$$

$$\begin{pmatrix} \frac{(2-k)\sigma_{res}}{3} & 0 & 0 \\ 0 & \frac{(2-k)\sigma_{res}}{3} & 0 \\ 0 & 0 & \frac{-(1+k)\sigma_{res}}{3} \end{pmatrix}$$

Furthermore, if $\sigma_z$ in the Equation 26 and the plastic constraint factor $\Psi$ of the first embodiment are used, the deviator stress that causes plastic deformation in an indentation direction can be expressed as Equation 27 and is equal to a value which results from division of load variation by contact area.

$$\frac{1}{\Psi} \frac{\Delta L}{A_s} = \frac{1+p}{3} \sigma_{res} \quad \text{[Equation 27]}$$

wherein $\Psi$ is a plastic constraint factor, which means a ratio of average contact pressure to genuine stress in an ideal plastic region, and is defined as 3.0 in the case of metals. (D. Tabor; "*The Hardness of Metals*" Clarendon Press, Oxford, UK (1951), recommending assumption of p as ⅓ in the case of a steel weldment.)

If both sides of Equation 27 are modified in the same manner as in Equation 25, the proportional constant $\eta_2$ to determine anisotropic biaxial residual stress can be defined as expressed in Equation 22.

$$\eta_2 = \frac{1}{\Psi}\frac{3}{(1+p)} \qquad \text{[Equation 28]}$$

The normal residual stress of the measured residual stress is determined as $p\sigma_{res}$ by Equation 27.

Figure 16:
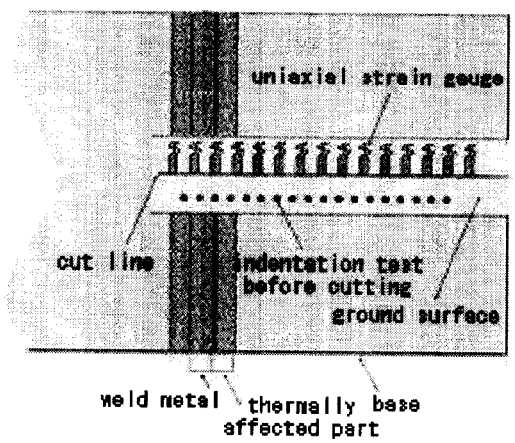
FIG. 16 is a view illustrating a method of inspecting an actual weldment through a cutting technique and a continuous indentation technique.
Figure 17:
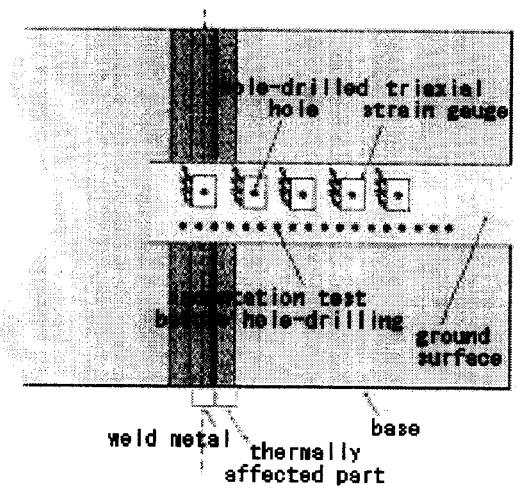
FIG. 17 is a view illustrating a method of inspecting an actual weldment through a hole-drilling technique and a continuous indentation technique.
Figure 18:
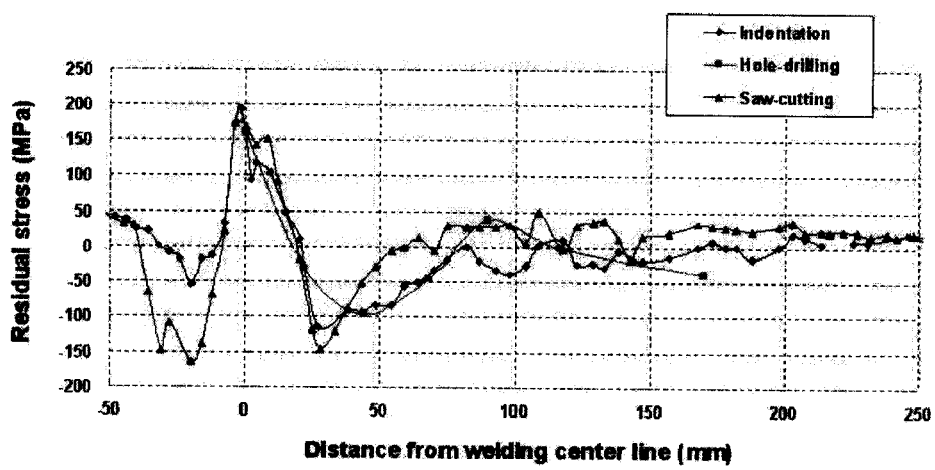
FIG. 18 is a graph illustrating comparison results of residual stress of API X65, which were measured respectively through the continuous indentation technique, the hole-drilling technique and the cutting technique.
Figure 19:
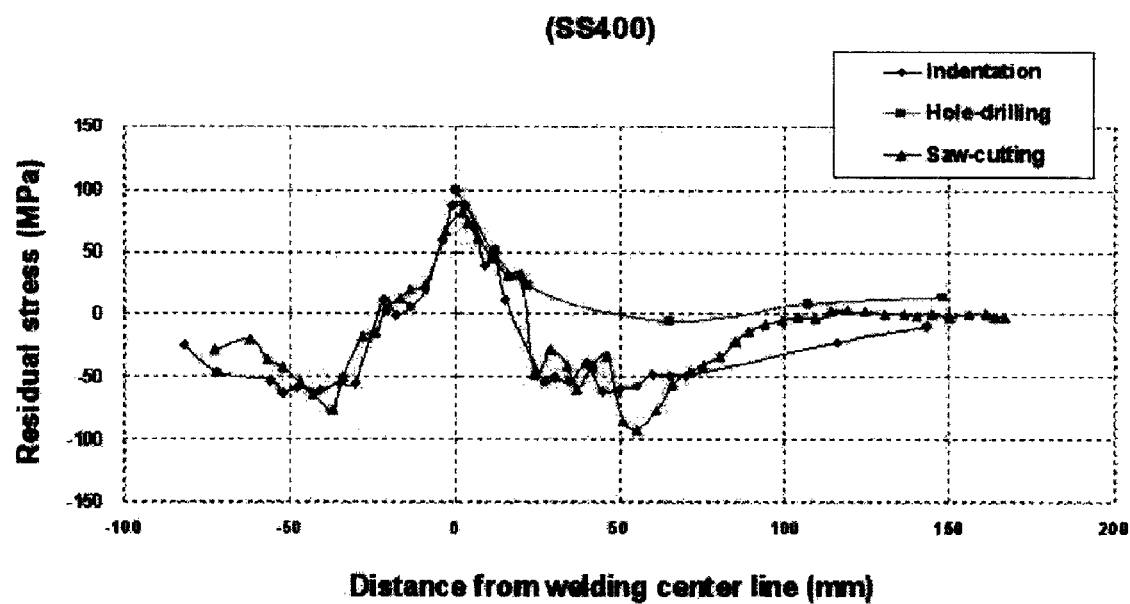
FIG. 19 is a graph illustrating comparison results of residual stress of SS400, which were measured respectively through the continuous indentation technique, the hole-drilling technique and the cutting technique.

FIGS. 16 and 17 are views illustrating residual stress measurement using the continuous indentation technique, hole-drilling technique, and saw-cutting technique respectively executed for API X65 and SS400. FIGS. 18 and 19 are graphs illustrating the comparison of residual stress measured through the above-mentioned measurement techniques. As shown in FIGS. 18 and 19, the values of residual stress measured using the continuous indentation technique, which is a nondestructive technique for measuring residual stress, is highly similar to the values measured using the hole-drilling technique or the saw-cutting technique, which is a destructive technique for measuring the residual stress.

Although the preferred embodiments of the present invention have been described above for illustrative purposes, those skilled in the art will appreciate that various modifications, additions and substitutions are possible, without departing from the scope and spirit of the invention as disclosed in the accompanying claims.

The invention claimed is:

1. A method of measuring residual stress of material using an instrumented indentation technique, comprising the steps of:
   repeatedly applying and removing an indentation load to and from a reference specimen of the material in a stress-free state, thus generating an indentation load-depth curve in a stress-free state; measuring a maximum indentation load and a maximum indentation depth from the indentation load-depth curve in a stress-free state; calculating an actual indentation depth ($h_c$) from the maximum indentation depth and calculating a contact area ($A_c$) from the actual indentation depth; and measuring hardness ($H_{IT}$) of the material from the contact area, thus generating a stress-free curve (stress reference curve) for the reference specimen;
   repeatedly applying and removing an indentation load to and from an actual specimen of the material in a stressed state, thus generating a stressed curve for the actual specimen; and
   measuring the residual stress of the material using both a load difference ($\Delta L$) obtained from comparison between the stress reference curve and the stressed curve and a contact area ($A_s$) in a stressed state obtained from a loading curve.

2. The method of measuring the residual stress of the material using the instrumented indentation technique according to claim 1, wherein an analysis of the indentation load-depth curve comprises:
   when the material is a base metal exclusive of a weldment, adapting a second-order equation expressed as $L = K_b^o(h+h_a)^2$ to the analysis,
   wherein the superscript o means a stress-free state, the subscript b means the base metal, and $k^o_b$ is a slope of a loading curve in a stress-free curve (stress reference curve) of the base metal, and
   $\Delta h_a$ is a tip compensation constant, which is a geometrical factor expressing a tip that is not an ideally sharp tip, that is, has become blunt, and so $\Delta h_a$ means a difference between an indentation depth when an ideally sharp tip is used and an indentation depth when an actual tip is used; and
   the step of measuring the maximum load and the maximum indentation depth comprises:
   finding a point of an actual maximum load ($L_{max}$) at each loading step in the indentation load-depth curve, and a point of an actual maximum indentation depth ($h_{max}$) at each unloading step in the indentation load-depth curve.

3. The method of measuring the residual stress of the material using the instrumented indentation technique according to claim 1, wherein an analysis of the indentation load-depth curve comprises:
   when the material is a weldment, adapting a second-order equation expressed as $L = K_w^o(h+\Delta h_a)^2$ to the analysis,
   wherein the superscript o means a stress-free state, the subscript w means the weldment, and $k^o_w$ is a slope of a loading curve in a stress-free curve (stress reference curve) of the weldment, and
   $\Delta h_a$ is a tip compensation constant, which is a geometrical factor expressing a tip that is not an ideally sharp a tip, that is, has become blunt, and so $\Delta h_a$ means a difference between a depth when an ideally sharp tip is used and a depth when an actual tip is used; and
   the step of measuring the maximum load and the maximum indentation depth comprises:
   finding a point of an actual maximum load ($L_{max}$) at each loading step in the indentation load-depth curve, and a point of an actual maximum depth ($h_{max}$) at each unloading step in the indentation load-depth curve.

4. The method of measuring the residual stress of the material using the instrumented indentation technique according to claim 3, wherein $k_w^o$ is expressed as the equation $$k_w^o = \frac{H_{IT,o}^W}{H_{IT,o}^b}k_b^o = \frac{\sigma_{IT}^w}{\sigma_{IT}^b}k_b^o$$

wherein $k^o_b$ is a slope of a loading curve in a stress reference curve (stress-free curve) of a base metal, $H^b_{IT,0}$ and $H^w_{IT,0}$ are hardness of the base metal and hardness of the weldment, respectively, and $\sigma^b_{IT}$ and $\sigma^w_{IT}$ are strengths of the base metal and the weldment, respectively.

5. The method of measuring the residual stress of the material using the instrumented indentation technique according to claim 4, wherein the strength of each of the base metal and the weldment is a yield strength ($\sigma_{IT,YS}$), a tensile strength ($\sigma_{IT,UTS}$), an average strength ($\sigma_{IT,f}$), or an indentation strength ($\sigma_{IT,r}$).

6. The method of measuring the residual stress of the material using the instrumented indentation technique according to claim 5, wherein the average strength ($\sigma_{IT,f}$) is an arithmetic average of the yield strength ($\sigma_{IT,YS}$) and the tensile strength ($\sigma_{IT,UTS}$), and
   the indentation strength ($\sigma_{IT,r}$) is a strength value corresponding to a modulus of strain, which is 0.08, in an indentation flow curve obtained through KS B 0950.

7. The method of measuring the residual stress of the material using the instrumented indentation technique according to claim 2 or 3, wherein the step of calculating the actual indentation depth ($h_c$) from the maximum indentation depth comprises:

adapting an equation expressed as $$h_c = f(h_{max} + \Delta h_a)$$

to the calculation, wherein $h_c$ is the real contact (indentation) depth, and f is a compensation constant of a ratio of the actual contact (indentation) depth to the maximum indentation depth ($h_{max}$) measured using a sensor.

8. The method of measuring the residual stress of the material using the instrumented indentation technique according to claim 7, wherein the compensation constant f is a ratio of the actual indentation depth ($h_c$) to the maximum indentation depth ($h_{max}$) measured using the sensor, and is expressed as an equation $$f = \frac{h_c}{h_{max} + \Delta h_a}, \text{ and}$$

actually, due to pile-up or sink-in of the material, a part of a surface of the material, with which the indenter tip is in contact, is raised or depressed, so that the actual indentation depth ($h_c$) varies, and so the compensation constant f to compensate for the variation is expressed as an equation $$f = 1.2445(1 - 0.6n)\left(1 - 7.2\frac{\sigma_{IT,YS}}{E_r}\right),$$

wherein $E_r$ is a reduced modulus of elasticity, n is a modulus of strain hardening of the material, and the compensation constant f ranges from 0.94 to 1.12.

9. The method of measuring the residual stress of the material using the instrumented indentation technique according to claim 7, wherein the step of calculating the actual contact area ($A_c$) from the actual contact (indentation) depth ($h_c$) uses an equation $$A_c = 24.5 h_c^2,$$

wherein $h_c$ is the actual contact (indentation) depth.

10. The method of measuring the residual stress of the material using the instrumented indentation technique according to claim 9, wherein the step of calculating the indentation hardness ($H_{IT}$) from the actual contact area ($A_c$) uses an equation $$H_{IT} = \frac{L_{max}}{A_C},$$

wherein $L_{max}$ is the actual maximum load in each loading step and $A_c$ is the actual contact area.

11. The method of measuring the residual stress of the material using the continuous indentation technique according to claim 1, wherein the step of generating the stressed curve for the actual specimen of the material in a stressed state through the instrumented indentation test comprises:

calculating the actual maximum load ($L_{max}$) at each loading step and the maximum indentation depth ($h_{max}$) that is the maximum displacement at each unloading step in the continuous indentation test for the actual specimen, and calculating slopes ($k_s^b$, $k_s^w$) of the loading curve in a stressed state from the loading curve.

12. The method of measuring the residual stress of the material using the instrumented indentation technique according to claim 1, wherein the load difference is a difference between a Load ($L^T$ or $L^c$) applied at a maximum indentation depth in the stressed curve (a slope of the loading curve in a stressed state) and a load ($L^o$) applied at the same maximum indentation depth in the stress-free curve (a slope of the loading curve in a stress-free state), and the contact area is calculated using an equation $$A_s^T = \frac{L_s^T}{H_{IT}} \text{ or } A_s^C = \frac{L_s^C}{H_{IT}},$$

wherein $A^T_S$ and $A^C_S$ are contact areas in a stressed state (tensile stressed state, compressive stressed state), and $H_{IT}$ is the indentation hardness.

13. The method of measuring the residual stress of the material using the instrumented indentation technique according to claim 2, wherein the residual stress of the base metal is expressed as an equation $$\sigma_{res} = \eta_1 \frac{\Delta L}{A_s},$$

wherein $\sigma_{res}$ is the residual stress, $\Delta L$ is a normal load difference induced from the stress-free curve and the stressed curve, $A_s$ is the contact area in a stressed state, and $\eta_1$ is a proportional constant to determine isotropic residual stress.

14. The method of measuring the residual stress of the material using the instrumented indentation technique according to claim 3, wherein the residual stress of the weldment is expressed as an equation $$\sigma_{res} = \eta_2 \frac{\Delta L}{A_s},$$

wherein $\sigma_{res}$ is the residual stress, $\Delta L$ is a normal load difference induced from the stress-free curve and the stressed curve, $A_s$ is the contact area in the stressed state, and $\eta_2$ is a proportional constant to determine anisotropic residual stress.

* * * * *